United States Patent
Sasaki et al.

(10) Patent No.: US 10,607,366 B2
(45) Date of Patent: Mar. 31, 2020

(54) INFORMATION PROCESSING APPARATUS, INFORMATION PROCESSING METHOD, AND NON-TRANSITORY STORAGE MEDIUM

(71) Applicant: CANON KABUSHIKI KAISHA, Tokyo (JP)

(72) Inventors: Shoya Sasaki, Yokohama (JP); Kenichi Nagae, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/889,660

(22) Filed: Feb. 6, 2018

(65) Prior Publication Data

US 2018/0225841 A1    Aug. 9, 2018

(30) Foreign Application Priority Data

Feb. 9, 2017   (JP) .................... 2017-022468

(51) Int. Cl.
  *G06T 7/70* (2017.01)
  *A61B 5/00* (2006.01)
(52) U.S. Cl.
  CPC .............. *G06T 7/70* (2017.01); *A61B 5/0095* (2013.01); *A61B 2576/00* (2013.01); *G06T 2207/10136* (2013.01); *G06T 2207/30196* (2013.01)
(58) Field of Classification Search
  CPC ..... A61B 5/0095; A61B 2576/00; G06T 7/70; G06T 2207/10136; G06T 2207/30196
  See application file for complete search history.

(56) References Cited

U.S. PATENT DOCUMENTS

| 8,016,419 B2* | 9/2011 | Zhang .................. A61B 5/0059 351/200 |
| 8,353,830 B2* | 1/2013 | Kanayama ........... A61B 5/0091 600/437 |

(Continued)

FOREIGN PATENT DOCUMENTS

| EP | 2799006 A1 | 11/2014 |
| JP | 2013-188461 A | 9/2013 |

OTHER PUBLICATIONS

Zhenyuan Yang, Jianhua Chen, Junjie Yao, Riqiang Lin, Jing Meng, Chengo Liu, Jinhua Yang, Xiang Li, Lihong Wang, and Liang Song, "Multi-parametric Quantitative Microvascular Imaging with Optical-resolution Photoacoustic Microscopy In Vivo," Optics Express, vol. 22, No. 2, pp. 1500-1511, Jan. 15, 2014. Document No. XP055484788.

(Continued)

*Primary Examiner* — Philip P. Dang
(74) *Attorney, Agent, or Firm* — Canon U.S.A., Inc. IP Division

(57) ABSTRACT

An information processing apparatus includes a first image acquisition unit configured to acquire first image data derived from a photoacoustic wave generated by light irradiation, a position acquisition unit configured to acquire position information indicating a position in the first image data having an image value that is within a predetermined range, a neighborhood position acquisition unit configured to acquire neighborhood position information indicating a neighborhood position neighboring the position based on the position information, and a display control unit configured to cause a display unit to display an image based on the first image data, the position information, and the neighborhood position information.

17 Claims, 10 Drawing Sheets

(56) References Cited

U.S. PATENT DOCUMENTS

| | | | | |
|---|---|---|---|---|
| 9,037,217 B1* | 5/2015 | Peyman | A61B 18/20 600/427 |
| 9,125,591 B2* | 9/2015 | Nanaumi | A61B 5/0073 |
| 9,128,032 B2* | 9/2015 | Carson | A61B 5/0059 |
| 9,217,703 B2* | 12/2015 | Zharov | A61B 5/0059 |
| 9,220,415 B2* | 12/2015 | Mandelis | A61B 5/0095 |
| 9,270,966 B2* | 2/2016 | Suzuki | H04N 9/87 |
| 9,339,254 B2* | 5/2016 | Wanda | A61B 5/14542 |
| 9,442,095 B2* | 9/2016 | Jiao | G01N 29/0681 |
| 9,510,974 B1* | 12/2016 | Peyman | A61F 9/00821 |
| 9,513,262 B2* | 12/2016 | Watanabe | G01N 29/0654 |
| 9,519,980 B2* | 12/2016 | Oishi | G06T 11/00 |
| 9,579,027 B2* | 2/2017 | Irisawa | A61B 5/0095 |
| 9,615,751 B2* | 4/2017 | Fukutani | A61B 5/0095 |
| 9,691,150 B2* | 6/2017 | Miyasa | G06T 7/33 |
| 9,730,589 B2* | 8/2017 | Tanaka | A61B 5/0095 |
| 9,763,578 B2* | 9/2017 | Tanaka | A61B 5/743 |
| 9,782,081 B2* | 10/2017 | Oyama | A61B 5/0095 |
| 9,867,545 B2* | 1/2018 | Sato | A61B 5/0095 |
| 9,931,171 B1* | 4/2018 | Peyman | A61B 34/35 |
| 9,943,231 B2* | 4/2018 | Furukawa | A61B 5/004 |
| 10,180,347 B2* | 1/2019 | Nakajima | G01H 9/00 |
| 2004/0258305 A1 | 12/2004 | Burnham | |
| 2013/0016185 A1* | 1/2013 | Stolka | A61B 1/041 348/46 |
| 2013/0116536 A1* | 5/2013 | Sato | A61B 5/748 600/407 |
| 2013/0218024 A1* | 8/2013 | Boctor | A61B 34/20 600/476 |
| 2013/0237802 A1 | 9/2013 | Irisawa | |
| 2015/0031990 A1* | 1/2015 | Boctor | A61B 8/483 600/424 |
| 2015/0148652 A1* | 5/2015 | Wanda | A61B 5/0095 600/407 |
| 2015/0235085 A1 | 8/2015 | Goto | |
| 2015/0282716 A1* | 10/2015 | Smeltzer | G01N 33/569 600/431 |
| 2015/0297177 A1* | 10/2015 | Boctor | A61B 8/4218 600/437 |
| 2016/0058295 A1* | 3/2016 | Imai | A61B 5/0095 600/407 |
| 2016/0135688 A1* | 5/2016 | Ebisawa | A61B 5/0095 600/407 |
| 2016/0139251 A1* | 5/2016 | Imai | G01S 7/52004 367/135 |
| 2016/0144402 A1* | 5/2016 | Kandori | B06B 1/0292 73/632 |
| 2016/0150973 A1* | 6/2016 | Abe | A61B 5/0095 600/409 |
| 2016/0174849 A1* | 6/2016 | Nanaumi | A61B 5/0095 600/407 |
| 2016/0206246 A1* | 7/2016 | Baba | A61B 5/0095 |
| 2016/0213259 A1* | 7/2016 | Wanda | A61B 5/0095 |
| 2016/0228009 A1* | 8/2016 | Tokita | A61B 8/4209 |
| 2016/0291217 A1* | 10/2016 | Furukawa | G02B 5/0263 |
| 2016/0296120 A1* | 10/2016 | Miyasa | A61B 5/0095 |
| 2016/0331347 A1* | 11/2016 | Ebisawa | A61B 8/4281 |
| 2016/0345837 A1* | 12/2016 | Takama | A61B 6/0414 |
| 2016/0345838 A1* | 12/2016 | Kanazaki | A61B 5/0095 |
| 2017/0030866 A1* | 2/2017 | Yamamoto | G01N 29/223 |
| 2017/0035361 A1* | 2/2017 | Yamamoto | A61B 5/0095 |
| 2017/0042429 A1* | 2/2017 | Nakajima | A61B 5/0095 |
| 2017/0052254 A1* | 2/2017 | Tateyama | G01S 15/8965 |
| 2017/0055843 A1* | 3/2017 | Umezawa | A61B 5/744 |
| 2017/0055844 A1* | 3/2017 | Umezawa | A61B 5/744 |
| 2017/0065181 A1* | 3/2017 | Masaki | A61B 8/08 |
| 2017/0067994 A1* | 3/2017 | Tanaka | A61B 8/4483 |
| 2017/0071475 A1* | 3/2017 | Irisawa | A61B 1/00006 |
| 2017/0086679 A1* | 3/2017 | Sekiya | A61B 5/0095 |
| 2017/0095155 A1* | 4/2017 | Nakajima | A61B 5/0035 |
| 2017/0164839 A1* | 6/2017 | Kandori | A61B 5/6843 |
| 2017/0181638 A1* | 6/2017 | Nanaumi | A61B 5/0095 |
| 2017/0181727 A1* | 6/2017 | Fukutani | A61B 5/0095 |
| 2017/0209119 A1* | 7/2017 | Masaki | A61B 5/0095 |
| 2017/0215739 A1* | 8/2017 | Miyasato | A61B 5/0095 |
| 2017/0215740 A1* | 8/2017 | Nakajima | A61B 5/0095 |
| 2017/0224223 A1* | 8/2017 | Nishihara | A61B 5/708 |
| 2017/0234790 A1* | 8/2017 | Kruger | G01N 21/1702 356/72 |
| 2017/0242096 A1* | 8/2017 | Okano | A61B 5/0046 |
| 2017/0273568 A1* | 9/2017 | Miyasato | A61B 5/0095 |
| 2017/0319077 A1* | 11/2017 | Nagao | A61B 8/429 |
| 2018/0014732 A1* | 1/2018 | Sekiya | A61B 5/72 |
| 2018/0020920 A1* | 1/2018 | Ermilov | A61B 5/0035 600/317 |
| 2018/0204349 A1* | 7/2018 | Ishikawa | A61B 5/7207 |
| 2018/0270474 A1* | 9/2018 | Liu | G06K 9/00201 |
| 2018/0289335 A1* | 10/2018 | Umezawa | A61B 5/7203 |
| 2018/0310831 A1* | 11/2018 | Cheng | A61B 34/20 |
| 2018/0310915 A1* | 11/2018 | Maruyama | A61B 8/14 |
| 2019/0038137 A1* | 2/2019 | Amano | A61B 5/743 |

OTHER PUBLICATIONS

Jadwiga Rogowska, "Digital Image Processing Techniques for Speckle Reduction, Enhancement, and Segmentation of Optical Coherence Tomography (OCT) Images," Optical Coherence Tomography: Principles and Applications, pp. 305-329, Aug. 25, 2006. Document No. XP055485227.

* cited by examiner

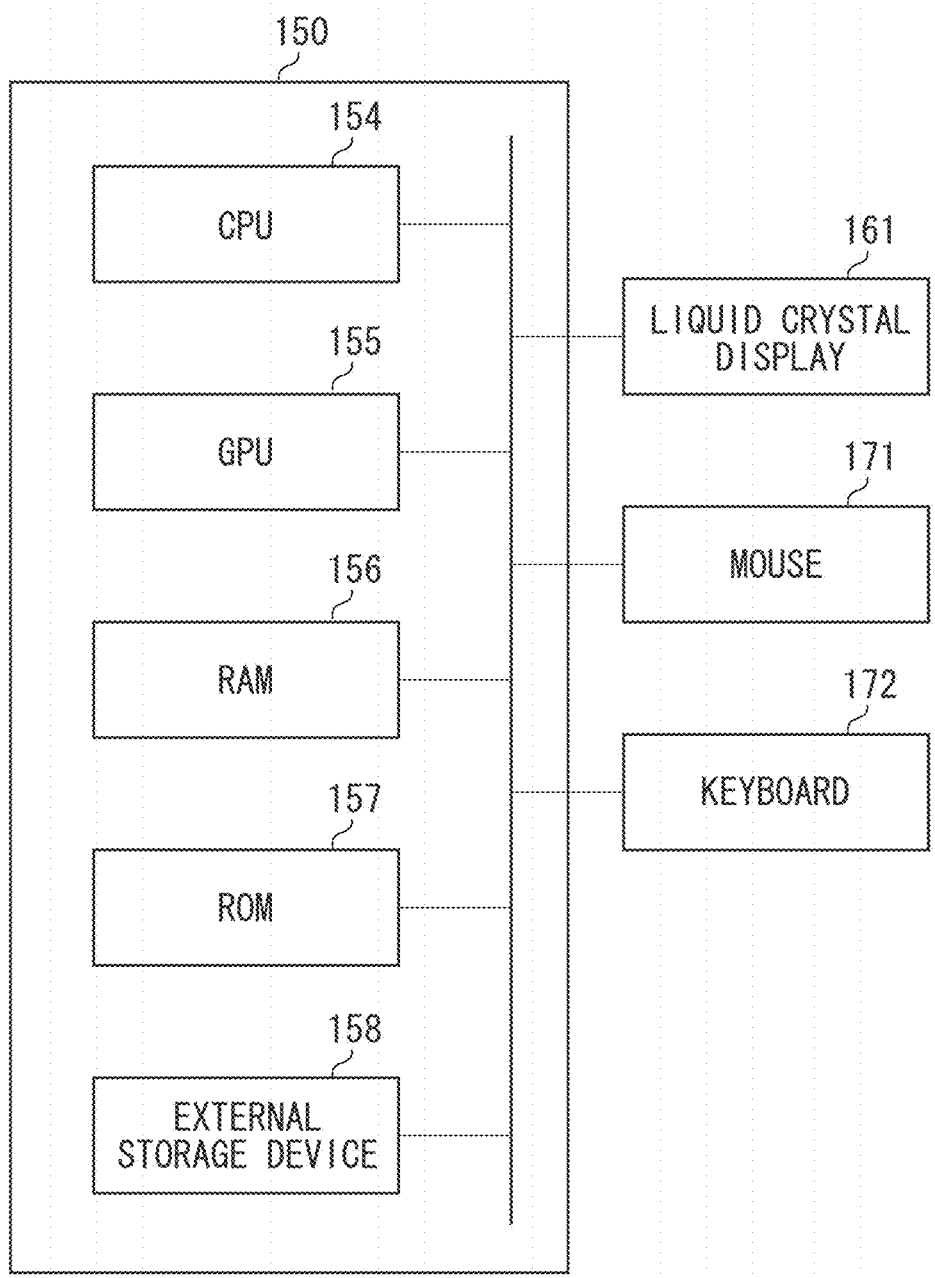

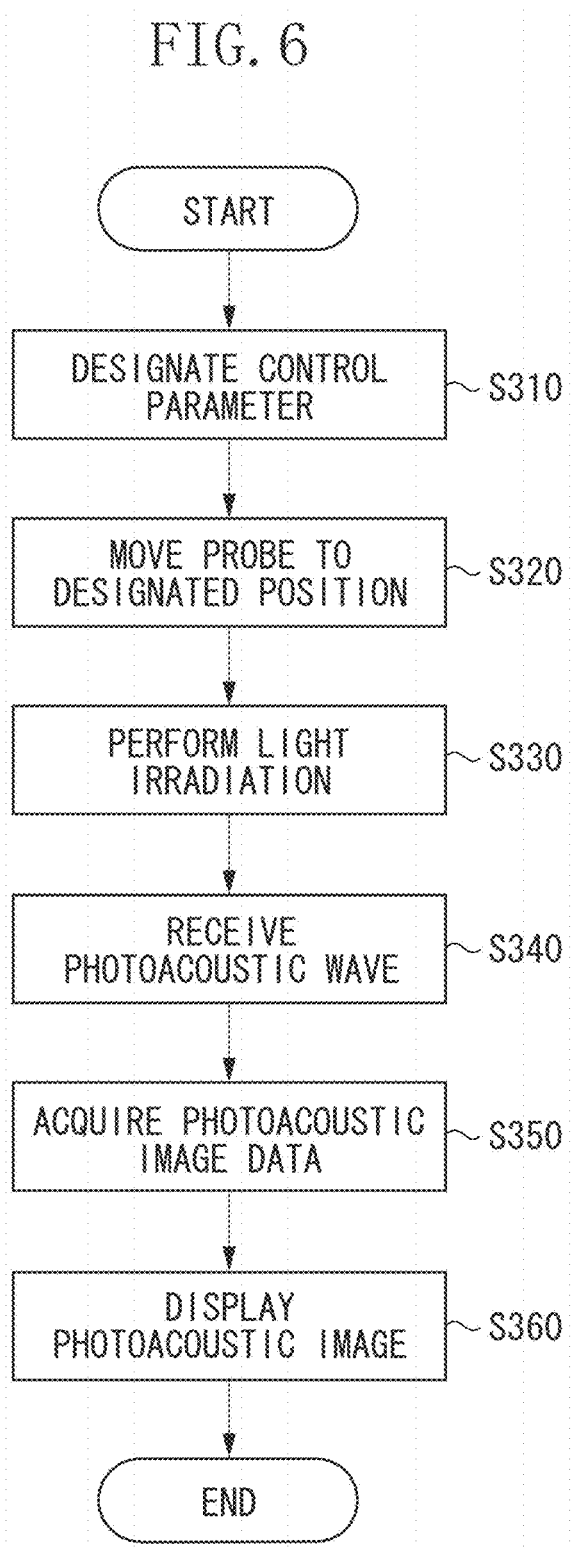

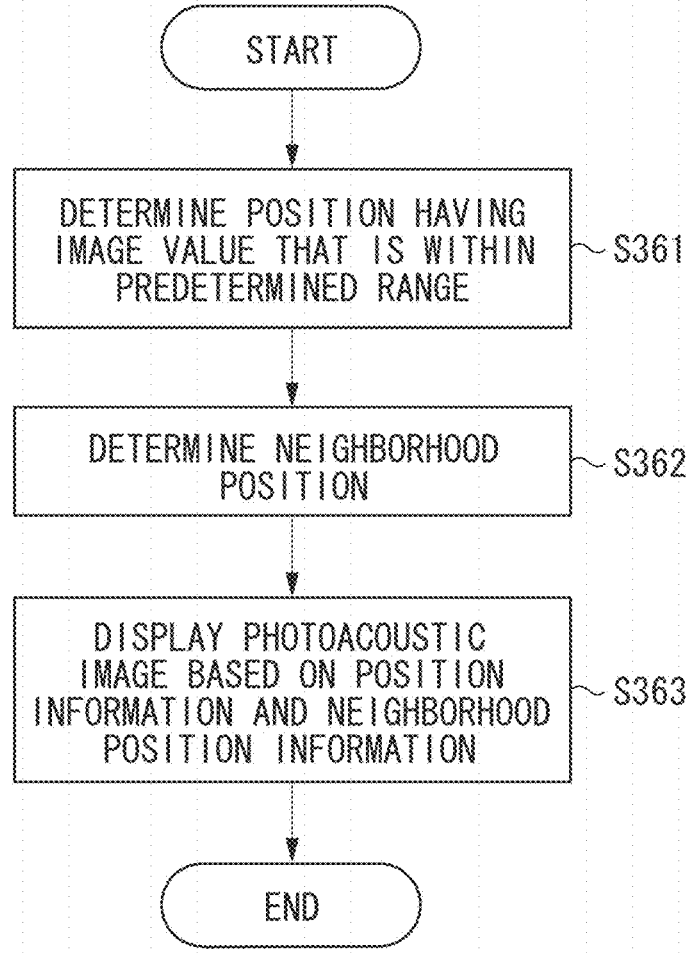

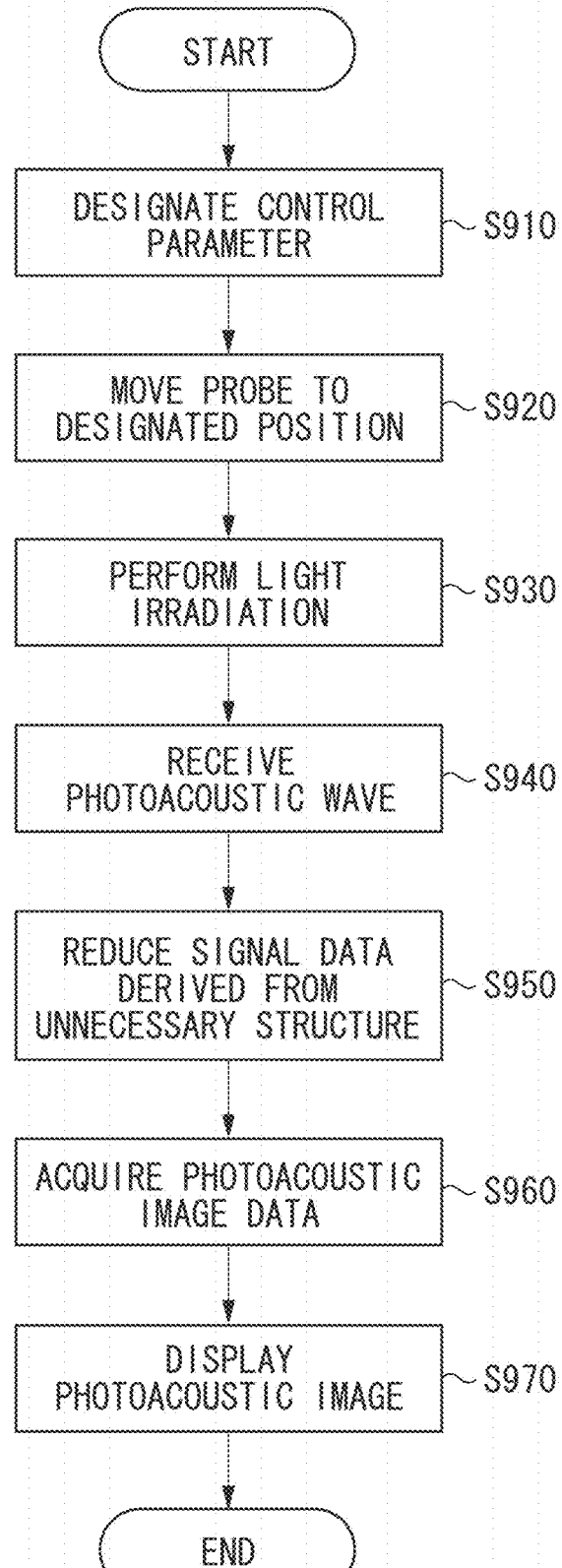

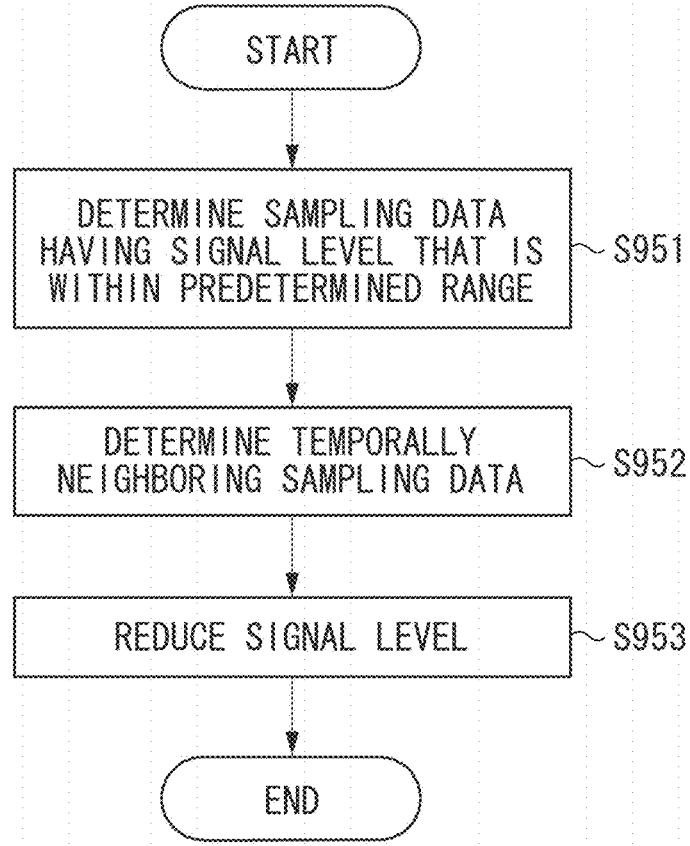

INFORMATION PROCESSING APPARATUS, INFORMATION PROCESSING METHOD, AND NON-TRANSITORY STORAGE MEDIUM

BACKGROUND OF THE INVENTION

Field of the Invention

The present invention relates to an information processing apparatus configured to acquire image data derived from a photoacoustic wave generated by light irradiation.

Description of the Related Art

Photoacoustic apparatuses that irradiate a subject such as a living body with pulsed light, and display a photoacoustic image indicating information about the inside of the subject based on an acoustic wave (also referred to as "photoacoustic wave") generated by photoacoustic effect are known.

In general, body hair and moles on the skin or epidermal layers have a high light absorptive capacity. Thus, photoacoustic waves generated from body hair and moles irradiated with pulsed light are likely to be greater than those produced from other regions of the subject. This results in large image values of the body hair and moles on photoacoustic images to decrease the visibility of observation regions.

Japanese Patent Application Laid-Open No. 2013-188461 discusses a display method in which a surface neighborhood area of a subject is detected based on a detected signal of a photoacoustic wave and information on the surface neighborhood area is attenuated to display an image with the attenuated surface neighborhood area.

However, in the display method discussed in Japanese Patent Application Laid-Open No. 2013-188461, information on an observation region in the surface neighborhood area may also be lost in addition to information about other regions, such as body hair and moles in the surface neighborhood area, that are not the observation regions. In this case, the visibility of the observation region in the surface neighborhood area decreases.

SUMMARY OF THE INVENTION

The present invention is directed to an information processing apparatus capable of generating and displaying a photoacoustic image of an observation region with high visibility.

According to an aspect of the present invention, an information processing apparatus includes a first image acquisition unit configured to acquire first image data derived from a photoacoustic wave generated by light irradiation, a position acquisition unit configured to acquire position information indicating a position in the first image data having an image value that is within a predetermined range, a neighborhood position acquisition unit configured to acquire neighborhood position information indicating a neighborhood position neighboring the position based on the position information, and a display control unit configured to cause a display unit to display an image based on the first image data, the position information, and the neighborhood position information.

Further features of the present invention will become apparent from the following description of exemplary embodiments with reference to the attached drawings.

BRIEF DESCRIPTION OF THE DRAWINGS

FIG. 5 is a block diagram illustrating a computer and its peripheral configuration according to the first exemplary embodiment.

FIG. 6 is a flowchart illustrating a subject information acquisition method according to the first exemplary embodiment.

FIG. 7 is a flowchart illustrating an image processing method according to the first exemplary embodiment.

FIG. 9 is a flowchart illustrating a subject information acquisition method according to a second exemplary embodiment.

FIG. 10 is a flowchart illustrating a signal processing method according to the second exemplary embodiment.

DESCRIPTION OF THE EMBODIMENTS

Various exemplary embodiments, features, and aspects of the invention will be described in detail below with reference to the drawings. Each of the embodiments of the present invention described below can be implemented solely or as a combination of a plurality of the embodiments or features thereof where necessary or where the combination of elements or features from individual embodiments in a single embodiment is beneficial.

In an image processing method according to a first exemplary embodiment, a position having an image value that is within a predetermined range in photoacoustic image data is determined. Then, the structure present in the position as well as structures present in neighborhood positions are judged unnecessary structures, and a photoacoustic image is displayed. The following describes an image processing method according to a comparative example and the image processing method according to the present exemplary embodiment.

First, the image processing method according to the comparative example will be described below with reference to FIGS. 1A, 1B, 1C, 1D, 1E, and 1F. As described above, photoacoustic waves generated from body hair and moles are likely to be greater than those produced from other regions of the subject. Thus, if the image value of a position is within a numerical value range that is larger than a predetermined threshold value, the image of the position is likely to be an unnecessary image (image of body hair or mole). In this way, the image of the position having the image value that is within the predetermined range is judged an unnecessary image.

Figure 1A:
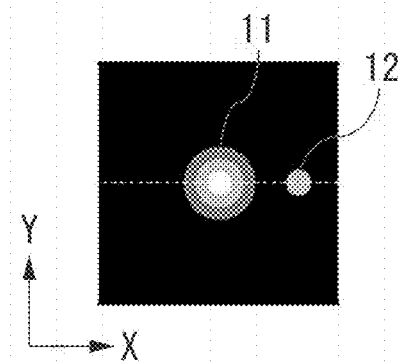
FIGS. 1A, 1B, 1C, 1D, 1E, and 1F illustrate an image processing method according to a comparative example.

FIG. 1A illustrates photoacoustic image data derived from a photoacoustic wave. In the photoacoustic image data illustrated in FIG. 1A, blacker positions have smaller image values, whereas whiter positions have larger image values. An image 11 is an image of body hair that is an unnecessary structure, and an image 12 is an image of a blood vessel that is an observation region.

Figure 1B:

FIG. 1B illustrates profiles of the image values in an x-axis direction specified by a dotted line in FIG. 1A. A profile 21 corresponds to the image 11, and a profile corresponds to the image 12. From FIG. 1B, it is understood that the image value of the image 11 of the body hair is higher than the image value of the image 12 of the blood vessel. Further, in FIG. 1B, especially the image value of the central position of the body hair is large, and the image values of positions around the central position are smaller than the image value of the central position. Further, the image values of positions around the body hair are substantially the same as the image value of the blood vessel that is an observation region.

As the comparative example, a process of reducing the image values of positions that are within a predetermined range is applied to the photoacoustic image illustrated in FIG. 1A. In FIG. 1B, a dotted line 31 or 32 indicates a threshold value (threshold value 31 or 32), and in the comparative example, a process of replacing image values that are higher than the threshold value 31 or 32 with a representative value (which is zero in the comparative example) is executed.

Figure 1C:
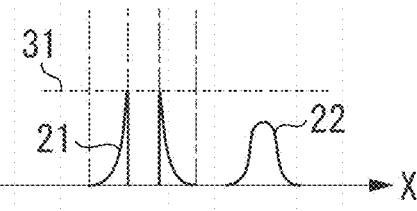
Figure 1D:
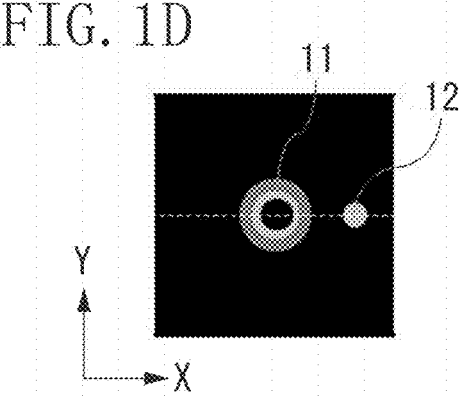

FIG. 1C illustrates profiles of the image values obtained by the process of replacing the image values that are higher than the threshold value 31 with zero. Further, FIG. 1D illustrates photoacoustic image data obtained by the process of replacing the image values that are higher than the threshold value 31 with zero. From FIGS. 1C and 1D, it is understood that the image processing is not capable of reducing most of the image 11 of the body hair. Thus, the effect of improving the visibility of the image 12 of the blood vessel that is an observation region is limited.

Figure 1E:
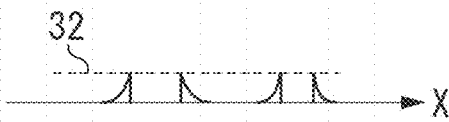
Figure 1F:
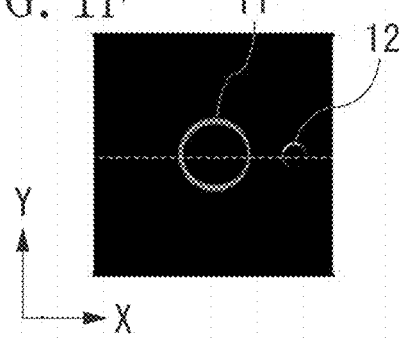

Next, FIG. 1E illustrates profiles of the image values obtained by a process of replacing the image values that are higher than the threshold value 32 with zero. FIG. 1F illustrates a photoacoustic image obtained by the process of replacing the image values that are higher than the threshold value 32 with zero. It is understood that the image processing is capable of reducing a wider area of the image 11 of the body hair, compared with FIGS. 1C and 1D. However, the image processing also reduces the image 12 of the blood vessel, so the visibility of the image 12 of the blood vessel that is an observation region decreases.

As described above as the comparative example, it is difficult to improve the visibility of an observation range solely with information about the positions having the image values that are within the predetermined range.

The present inventor conducted studies on the above-described problem and arrived at image processing capable of appropriately discriminating between observation regions and unnecessary structures based on image values of image data. The image processing according to the present exemplary embodiment will be described below with reference to FIGS. 2A, 2B, 2C, 2D, and 2E.

Figure 2A:
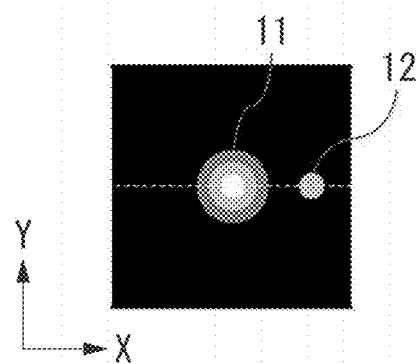
FIGS. 2A, 2B, 2C, 2D, and 2E illustrate an image processing method according to a first exemplary embodiment.
Figure 2B:
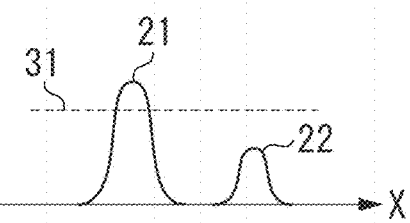

FIG. 2A illustrates photoacoustic image data acquired based on a photoacoustic wave as in FIG. 1A. FIG. 2B illustrates profiles of image values in the x-axis direction specified by a dotted line in FIG. 2A.

Figure 2C:
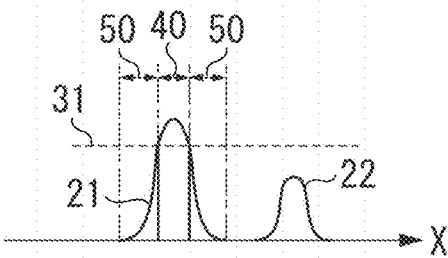

FIG. 2C illustrates profiles of image values indicating image values on which the image value reduction that is a feature of the image processing according to the present exemplary embodiment is to be executed. The image processing according to the present exemplary embodiment is characterized in that the image value reduction is executed on not only the image value of a position 40 that is higher than the threshold value 31 but also the image value of a position 50 neighboring the position 40.

Figure 2D:
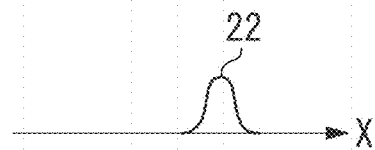

FIG. 2D illustrates a profile of image values obtained by replacing the image values of the position 40 and the position 50 neighboring the position 40 illustrated in FIG. 2C with zero. Further, FIG. 2E illustrates photoacoustic image data obtained by the image processing.

Figure 2E:
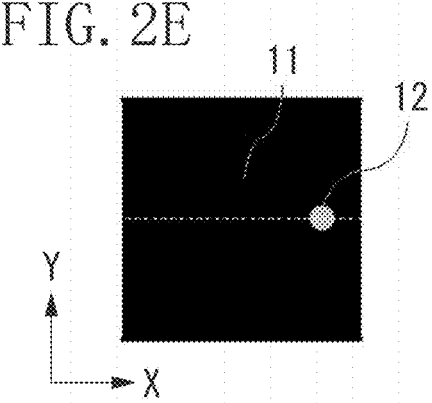

As illustrated in FIGS. 2D and 2E, the present exemplary embodiment is capable of selectively reducing most of the image 11 of the body hair that is an unnecessary image, compared with the comparative example. On the other hand, the image 12 of the blood vessel that is an observation region is less reduced in the present exemplary embodiment, compared with the comparative example. As described above, the present exemplary embodiment is capable of improving the visibility of the image 12 of the blood vessel that is an observation region, compared with the comparative example.

The present exemplary embodiment is directed to a technique for discriminating unnecessary structures based on image values of image data and performing displaying with improved visibility of observation regions. The visibility of observation regions can be improved by, for example, decreasing the lightness of unnecessary structures (increasing the transparency) or separately displaying unnecessary structures and observation regions.

Various exemplary embodiments of the present invention will be described below with reference to the drawings. It should be noted that the dimensions, materials, shapes, relative locations, etc. of components described below are to be changed as needed depending on the structure of an apparatus to which the invention is applied and various conditions and are not intended to limit the scope of the invention.

Photoacoustic images acquired by the photoacoustic apparatus according to the present exemplary embodiment are a concept including any images derived from photoacoustic waves generated by light irradiation. The photoacoustic images are image data indicating a spatial distribution of subject information about at least one of the sound pressure (initial sound pressure) at the time of photoacoustic wave generation, optical absorption energy densities of the photoacoustic waves, optical absorption coefficients of the photoacoustic waves, concentrations of substances included in the subject (oxygen saturation, etc.), etc.

The following describes the configuration of the photoacoustic apparatus and an information processing method according to the present exemplary embodiment.

Figure 3:
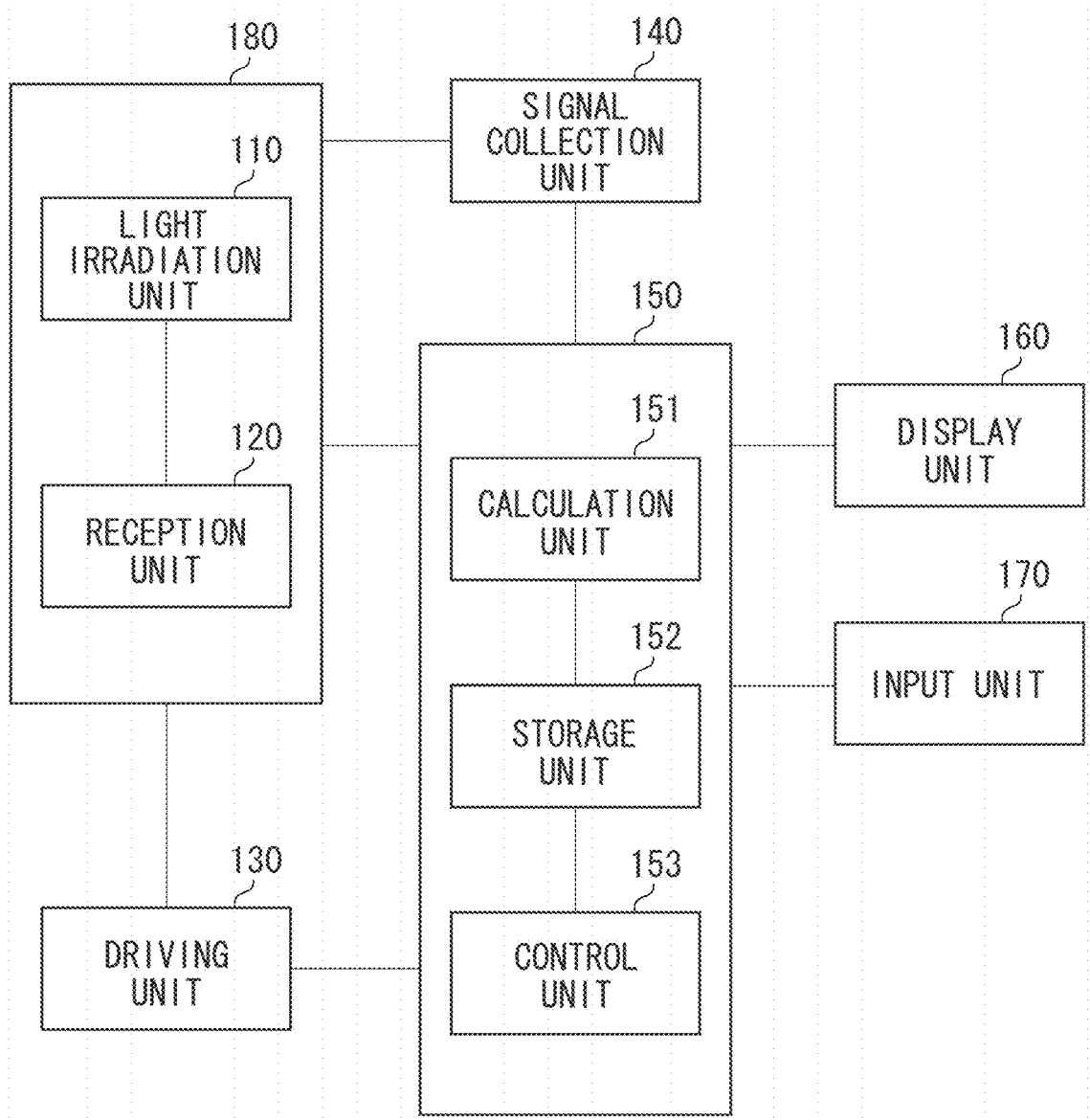
FIG. 3 is a block diagram illustrating a photoacoustic apparatus according to the first exemplary embodiment.
Figure 4:
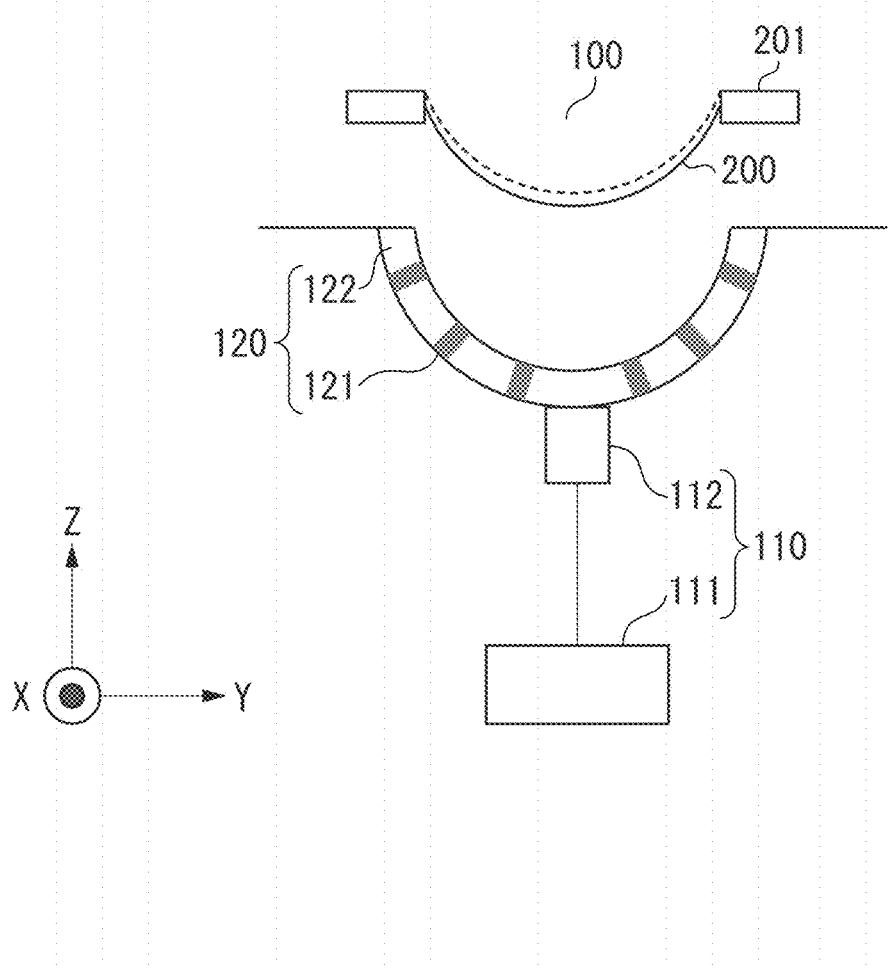
FIG. 4 schematically illustrates a probe according to the first exemplary embodiment.

The configuration of the photoacoustic apparatus according to the present exemplary embodiment will be described below with reference to FIG. 3. FIG. 3 is a schematic block diagram illustrating the entire photoacoustic apparatus. The photoacoustic apparatus according to the present exemplary embodiment includes a driving unit 130, a signal collection unit 140, a computer 150, a display unit 160, an input unit 170, and a probe 180. The probe 180 includes a light irradiation unit 110 and a reception unit 120. FIG. 4 schematically illustrates the probe 180 according to the present exemplary embodiment. A measurement target is a subject 100. The driving unit 130 drives the light irradiation unit 110 and the reception unit 120 to execute mechanical scans. The light irradiation unit 110 irradiates the subject 100 with light to generate an acoustic wave in the subject 100. The acoustic wave generated by the photoacoustic effect caused by light is also referred to as "photoacoustic wave". The reception unit 120 receives the photoacoustic wave to output an electric signal (photoacoustic signal) as an analog signal.

The signal collection unit 140 converts the analog signal output from the reception unit 120 into a digital signal and outputs the digital signal to the computer 150. The computer 150 stores the digital signal output from the signal collection unit 140 as signal data derived from the photoacoustic wave.

The computer 150 executes signal processing on the stored digital signal to generate image data representing a photoacoustic image. Further, the computer 150 executes image processing on the acquired image data and then outputs the image data to the display unit 160. The display unit 160 displays the photoacoustic image. A doctor or technologist as a user checks the photoacoustic image displayed on the display unit 160 to make a diagnosis. The displayed image is saved in a memory in the computer 150, a data management system connected to a modality via a network, etc. based on a save instruction from the user or the computer 150.

Further, the computer 150 also drives and controls configurations included in the photoacoustic apparatus. Further, the display unit 160 can display a graphical user interface (GUI), etc. besides the images generated by the computer 150. The input unit 170 is configured such that the user can input information. The user can perform an operation, such as an instruction to start or end measurement or an instruction to save a generated image, using the input unit 170.

In a subject information processing method according to the present exemplary embodiment, the image value of a position that is within the predetermined range and the image values corresponding to neighborhood positions neighboring the position in the generated image data are reduced to generate image data in which the image values of the position and the neighborhood positions are reduced, and the generated image data is displayed. In this way, portions other than an observation region, such as a body hair portion and a mole portion, on the images are reduced to improve the visibility of the observation region in the subject.

The components of the photoacoustic apparatus according to the present exemplary embodiment will be described in detail below.

(Light Irradiation Unit 110)

The light irradiation unit 110 includes a light source 111 and an optical system 112. The light source 111 emits light, and the optical system 112 guides the light emitted from the light source 111 to the subject 100. Examples of the light include pulsed light such as rectangular wave light and triangular wave light.

The pulse width of the light emitted from the light source 111 can be 1 ns or more and 100 ns or less. Further, the wavelength of the light can be in the range of about 400 nm to about 1600 nm. To image a blood vessel at high resolution, a wavelength (400 nm or more, 700 nm or less) that is absorbed significantly by blood vessels can be used. To image a deep portion of a living body, light having a wavelength (700 nm or more, 1100 nm or less) that is typically less absorbed by background tissue (water, fat, etc.) of the living body can be used.

A laser or a light emitting diode can be used as the light source 111. Further, to use light of a plurality of wavelengths in the measurement, a wavelength-changeable light source can be used. In the case of irradiating a subject with a plurality of wavelengths, a plurality of light sources that emit light beams having different wavelengths from each other can be prepared to emit light one after another. In the case in which a plurality of light sources is provided, the plurality of light sources is collectively referred to as the light source. As to the laser, various lasers can be used such as a solid-state laser, gas laser, dye laser, and semiconductor laser. For example, a pulse laser such as a neodymium-doped yttrium aluminum garnet (Nd:YAG) laser or alexandrite laser can be used as the light source. Further, a titanium-sapphire (Ti:sa) laser or optical parametric oscillators (OPO) laser using Nd:YAG laser light as excited light can be used as the light source. Further, a flash lamp or light emitting diode can be used as the light source 111. Further, a microwave source can be used as the light source 111.

Optical elements such as a lens, mirror, and optical fiber can be used in the optical system 112. In the case in which the subject 100 is a breast, etc., a light emission unit of the optical system 112 can include a diffusion plate that diffuses light to emit pulse light with an increased beam diameter. On the other hand, in a photoacoustic microscope, the light emission unit of the optical system 112 can include a lens, etc. to emit a focused beam so that the resolution is increased.

Alternatively, the light irradiation unit 110 can omit the optical system 112 and the light source 111 can directly irradiate the subject 100 with light.

(Reception Unit 120)

The reception unit 120 includes a transducer 121 and a support member 122. The transducer 121 receives an acoustic wave to output an electric signal, and the support member 122 supports the transducer 121. Further, the transducer 121 can be a transmission unit that transmits the acoustic wave. The transducer 121 as the reception unit and the transducer 121 as the transmission unit can be a single (common) transducer or separate transducers.

Examples of materials that can be used as materials of the transducer 121 include piezo-ceramic materials, such as lead zirconate titanate (PZT), and high-polymer piezoelectric film materials, such as polyvinylidene fluoride (PVDF). Further, an element other than piezoelectric elements can be used. For example, a capacitive micro-machined ultrasonic transducer (CMUT) or a transducer using a Fabry-Pérot interferometer can be used. Any transducers capable of receiving acoustic waves to output electric signals can be employed. Further, signals obtained by the transducers are time-resolved signals. More specifically, the amplitude of a signal obtained by a transducer represents a value based on the sound pressure received by the transducer at each time (e.g., a value that is proportional to the sound pressure).

Frequency components of the photoacoustic waves are typically 100 KHz to 100 MHz, and a transducer capable of detecting the frequencies is used as the transducer 121.

The support member 122 can be made of a metal material having high mechanical strength. To cause more irradiation light to enter a subject, the surface of the support member 122 on the subject 100 side can be treated to have a mirror-like surface or a light-scattering surface. In the present exemplary embodiment, the support member 122 has a hemispherical shell shape and is capable of supporting the plurality of transducers 121 on the hemispherical shell. In this case, directional axes of the transducers 121 located on the support member 122 are focused near the center of curvature of the hemisphere. Then, when an image is generated using the signals output from the plurality of transducers 121, the image quality near the center of curvature is high. The support member 122 can have any structure capable of supporting the transducers 121. The plurality of transducers can be arranged next to each other in a flat or curved surface of the support member 122, which is referred to as a 1-dimensional (1D) array, 1.5-dimensional (1.5D) array, 1.75-dimensional (1.75D) array, or 2-dimensional (2D) array. The plurality of transducers 121 corresponds to a plurality of reception units.

Further, the support member 122 can function as a container for storing acoustic matching materials. More specifically, the support member 122 can be used as a container for arranging an acoustic matching material between the transducer 121 and the subject 100.

Further, the reception unit 120 can include an amplifier that amplifies time-series analog signals output from the transducer 121. Further, the reception unit 120 can include an analog/digital (A/D) converter that converts the time-series analog signals output from the transducer 121 into time-series digital signals. More specifically, the reception unit 120 can include the signal collection unit 140 described below.

To detect acoustic waves from various angles, ideally the transducers 121 are arranged to completely surround the subject 100. When the subject 100 is so large that the transducers cannot be arranged to completely surround the subject 100, the transducers can be arranged on the support member 122 with the hemispherical shape to surround the subject 100 as completely as possible.

The locations and number of transducers and the shape of the support member are to be optimized according to the subject, and any reception unit 120 can be employed in the present exemplary embodiment.

The space between the reception unit 120 and the subject 100 is filled with a medium through which the photoacoustic waves can propagate. The medium uses a material through which the acoustic waves can propagate, which has consistent acoustic characteristics at interfaces with the subject 100 and the transducer 121, and which has the highest possible photoacoustic wave transmittance. For example, water or ultrasonic gel can be used as the medium.

FIG. 4 is a side view illustrating the probe 180. The probe 180 according to the present exemplary embodiment includes the reception unit 120 with the plurality of transducers 121 arranged three-dimensionally on the hemispherically-shaped support member 122 having an opening. Further, the light emission unit of the optical system 112 is arranged on a bottom portion of the support member 122.

In the present exemplary embodiment, as illustrated in FIG. 4, the subject 100 is brought into contact with a holding member 200 to hold the shape of the subject 100. In the present exemplary embodiment, the case in which the subject 100 is a breast and a bed supporting an examinee in prone position includes an opening through which the breast is inserted to measure the breast hanging from the opening in the vertical direction is considered.

The space between the reception unit 120 and the holding member 200 is filled with a medium through which the photoacoustic waves can propagate. The medium uses a material through which the acoustic waves can propagate, which has consistent acoustic characteristics at interfaces with the subject 100 and the transducer 121, and which has the highest possible photoacoustic wave transmittance. For example, water or ultrasonic gel can be used as the medium.

The holding member 200 as a holding unit is used to hold the shape of the subject 100 during the measurement. The holding member 200 holds the subject 100 to prevent the subject 100 from moving and to keep the position of the subject 100 within the holding member 200. A resin material such as polycarbonate, polyethylene, or polyethylene terephthalate can be used as a material of the holding member 200.

The holding member 200 is desirably made of a material that is hard enough to hold the subject 100. The holding member 200 can be made of a material that transmits light used for the measurement. The holding member 200 can be made of a material having the same impedance level as that of the subject 100. In the case in which the subject 100 has a curved surface, such as the breast, the holding member 200 can be formed to have a depressed portion. In this case, the subject 100 can be inserted into the depressed portion of the holding member 200.

The holding member 200 is attached to an attachment portion 201. The attachment portion 201 can be designed such that the holding member 200 can be replaced with a plurality of types of holding members 200 according to the size of the subject. For example, the attachment portion 201 can be designed such that the holding member 200 can be replaced with holding members having a different curvature radius, curvature center, etc.

(Driving Unit 130)

The driving unit 130 is a portion that changes the relative positions of the subject 100 and the reception unit 120. The driving unit 130 includes a motor, such as a stepping motor, a driving mechanism, and a position sensor. The motor generates driving force. The driving mechanism transmits the driving force. The position sensor detects position information about the reception unit 120. A leadscrew mechanism, a linkage mechanism, a gear mechanism, a hydraulic mechanism, etc. can be used as the driving mechanism. Further, a potentiometer using an encoder, a variable resistor, a linear scale, a magnetic sensor, an infrared sensor, an ultrasonic sensor, etc. can be used as the position sensor.

The driving unit 130 can change the relative positions of the subject 100 and the reception unit 120 not only in XY directions (two-dimensionally) but also one-dimensionally or three-dimensionally.

The driving unit 130 can change the relative positions of the subject 100 and the reception unit 120 by moving the subject 100 with the reception unit 120 fixed. In the case of moving the subject 100, the subject 100 can be moved by moving the holding member 200 that holds the subject 100. Further, both the subject 100 and the reception unit 120 can be moved.

The driving unit 130 can move the relative positions continuously or can move the relative positions by a step-and-repeat method. The driving unit 130 can be an electric stage that moves the relative positions along a programmed trajectory or can be a manual stage.

Further, while the driving unit 130 drives and scans the light irradiation unit 110 and the reception unit 120 at the same time in the present exemplary embodiment, the driving unit 130 can drive only the light irradiation unit 110 or only the reception unit 120.

(Signal Collection Unit 140)

The signal collection unit 140 includes an amplifier and an A/D converter. The amplifier amplifies electric signals that are analog signals output from the transducer 121. The A/D converter converts the analog signals output from the amplifier into digital signals. The signal collection unit 140 can include a field programmable gate array (FPGA) chip. The digital signals output from the signal collection unit 140 are stored in a storage unit 152 in the computer 150. The signal collection unit 140 is also referred to as a data acquisition system (DAS). As used herein, the term "electric signal" is a concept including analog signals and digital signals. Alternatively, a light detection sensor such as a photodiode can detect light emitted from the light irradiation unit 110 and the signal collection unit 140 can start the above-described processing in synchronization with the detection result as a trigger. Further, the signal collection unit 140 can start the above-described processing in synchronization with an instruction as a trigger that is given using a freeze button, etc.

(Computer 150)

The computer 150 as an information processing apparatus includes a calculation unit 151, the storage unit 152, and a control unit 153. Functions of the components will be described below in the description of processes.

A unit having a calculation function as the calculation unit 151 can include a processor, such as a central processing unit (CPU) or graphics processing unit (GPU), and a calculation circuit, such as a FPGA chip. The units can include a single processor and a single calculation circuit or a plurality of processors and a plurality of calculation circuits. The calculation unit 151 can receive from the input unit 170 various parameters, such as the sound speed of the subject 100 and the structure of the holding member 200, and execute processing on received signals.

The storage unit 152 can include a non-transitory medium such as a read-only memory (ROM), a magnetic disk, or a flash memory. Further, the storage unit 152 can be a volatile medium such as a random access memory (RAM). The storage medium to store programs is the non-transitory storage medium. The storage unit 152 can include a single storage medium or a plurality of storage mediums.

The storage unit 152 can store image data that represents a photoacoustic image generated by the calculation unit 151 by a method described below.

The control unit 153 includes a calculation device such as a CPU. The control unit 153 controls operations of the components of the photoacoustic apparatus. The control unit 153 can control the components of the photoacoustic apparatus in response to an instruction signal, such as a start of measurement, given by various operations from the input unit 170. Further, the control unit 153 reads program codes stored in the storage unit 152 to control operations of the components of the photoacoustic apparatus.

The computer 150 can be a specifically designed work station. Further, the components of the computer 150 can be different pieces of hardware. Further, at least a part of the components of the computer 150 can be a single piece of hardware.

FIG. 5 illustrates an example of a specific configuration of the computer 150 according to the present exemplary embodiment. The computer 150 according to the present exemplary embodiment includes a CPU 154, a GPU 155, a RAM 156, a ROM 157, and an external storage device 158. Further, a liquid crystal display 161 as the display unit 160 and a mouse 171 and a keyboard 172 as the input unit 170 are connected to the computer 150.

Further, the computer 150 and the plurality of transducers 121 can be contained in a common housing and provided. The computer contained in the housing can execute a part of the signal processing and a computer provided outside the housing can execute the rest of the signal processing. In this case, the computer contained in the housing and the computer provided outside the housing are collectively referred to as the computer according to the present exemplary embodiment. More specifically, the pieces of hardware of the computer do not have to be contained in a single housing.

(Display Unit 160)

The display unit 160 is a display such as a liquid crystal display or an organic electroluminescence (EL) display. The display unit 160 is a device that displays images based on image data acquired from the computer 150, numerical values of specific positions, etc. The display unit 160 can display a GUI for operating the images and the device. As to the display of the subject information, the subject information can be displayed after the display unit 160 or the computer 150 executes image processing on the subject information.

(Input Unit 170)

An operation console, such as a mouse and a keyboard, operable by the user can be employed as the input unit 170. Further, the display unit 160 can be a touch panel and used as the input unit 170.

The input unit 170 can be configured such that a predetermined range for image processing and displaying can be set and parameters for determining a spatial range to define neighborhood positions of a position that is within the predetermined range can be input. Further, the input unit 170 can be configured such that parameters relating to displaying can be input. As to an input method, numerical values can be input, or the parameters can be input by operating a slider bar. Further, an image displayed on the display unit 160 can be updated with an image to which various parameters changed according to a user instruction given with the input unit 170 are applied in response to the user instruction. In this way, the user can set the parameters as appropriate by checking an image generated based on the parameters determined by an operation of the user.

Further, the user can operate the input unit 170 located remotely from the photoacoustic apparatus, and information input using the input unit 170 can be transmitted to the photoacoustic apparatus via the network.

The components of the photoacoustic apparatus can be provided as separate components or can be integrated as a single apparatus. Further, at least a part of the components can be integrated as a single apparatus.

Further, the components of the photoacoustic apparatus transmit and receive information via wired or wireless transmission/reception.

(Subject 100)

The subject 100 will be described below although the subject 100 does not constitute the photoacoustic apparatus. The photoacoustic apparatus according to the present exemplary embodiment can be used for a diagnosis of a malignant tumor, blood vessel disease, etc. of a person or animal, chemical treatment follow-up, etc. Thus, the subject 100 is expected to be a diagnosis target region such as a living body, specifically the breast, organ, network of blood vessels, head part, neck part, abdominal part, extremities including the fingers and toes, etc. of a human body or animal. For example, if a human body is a measurement target, oxyhemoglobin, deoxyhemoglobin, a blood vessel containing large amounts of oxyhemoglobin and deoxyhemoglobin, a new blood vessel formed near a tumor, etc. can be set as a target of an optical absorber. Further, plaque on carotid arteries, etc. can be set as a target of the optical absorber. Further, melanin, collagen, lipid, etc. contained in skin, etc. can be set as a target of the optical absorber. Further, a dye such as methylene blue (MB) or indocyanine green (ICG), gold fine particles, or an externally-introduced substance obtained by integrating or chemically modifying the dye and gold fine particles can be set as the optical absorber. Further, a phantom representing a living body can be set as the subject 100.

(Process for Acquisition of Subject Information)

Next, steps included in a subject information acquisition method including information processing according to the present exemplary embodiment will be described below with reference to FIG. 6.

(Step S310: Control Parameter Designation)

The user designates using the input unit 170 control parameters, such as irradiation conditions (repeat frequency or wavelength, etc.) of the light irradiation unit 110 and the position of the probe 180, which are necessary to acquire subject information. The computer 150 sets the control parameters determined based on the user instruction.

(Step S320: Movement of Probe to Designated Position)

The control unit 153 causes the driving unit 130 to move the probe 180 to the designated position based on the control parameters designated in step S301. If image capturing in a plurality of positions is designated in step S310, the driving unit 130 first moves the probe 180 to the first designated position. Alternatively, the driving unit 130 can move the probe 180 to a position programmed in advance when a measurement start instruction is given. In the case of a hand-held probe, the user can hold and move the probe 180 to a desired position.

(Step S330: Light Irradiation)

The light irradiation unit 110 irradiates the subject 100 with light based on the control parameters designated in step S310.

The light generated from the light source 111 irradiates the subject 100 as pulsed light through the optical system 112. Then, the pulsed light is absorbed in the subject 100, and a photoacoustic wave is generated by the photoacoustic effect. The light irradiation unit 110 transmits a synchronization signal to the signal collection unit 140 concurrently with the transmission of the pulsed light.

(Step S340: Photoacoustic Wave Reception)

If the signal collection unit 140 receives the synchronization signal transmitted from the light irradiation unit 110, the signal collection unit 140 starts a signal collection operation. More specifically, the signal collection unit 140 executes amplification and A/D conversion on the analog electric signal derived from the acoustic wave, and output from the reception unit 120, to generate an amplified digital electric signal, and outputs the amplified digital electric signal to the computer 150. The computer 150 saves on the storage unit 152 the signal transmitted from the signal collection unit 140. If image capturing in a plurality of scan positions is designated in step S301, steps S320 to S340 are executed in each of the designated scan positions to repeat pulsed light irradiation and generation of digital signals derived from acoustic waves. Alternatively, the computer 150 can acquire position information about the reception unit 120 at the time of light emission based on the output from the position sensor of the driving unit 130, with the light emission being a trigger, and store the acquired position information.

(Step S350: Photoacoustic Image Data Acquisition)

The calculation unit 151 of the computer 150 as an image acquisition unit generates photoacoustic image data based on the signal data stored in the storage unit 152 and saves the generated photoacoustic image data in the storage unit 152. At this time, the computer 150 can generate photoacoustic image data based on the control parameters, such as the position of the probe 180, in addition to the signal data.

As to a reconstruction algorithm for converting signal data into volume data as a spatial distribution, an analytical reconstruction method, such as a time-domain back-projection method or Fourier-domain back-projection method, or a model-based method (repeat calculation method) can be employed. Examples of a time-domain back-projection method include universal back-projection (UBP), filtered back-projection (FBP), and delay-and-sum.

Further, the calculation unit 151 can acquire absorption coefficient distribution information by calculating the light fluence distribution of light in the subject 100 irradiated with the light and then dividing the initial sound pressure distribution by the light fluence distribution. In this case, the absorption coefficient distribution information can be acquired as photoacoustic image data. The computer 150 can calculate the light fluence spatial distribution in the subject 100 by a method of numerically solving a transfer equation or diffusion equation representing the light energy in a medium that absorbs and scatters light. As to the numerically solving method, a finite element method, a difference method, a Monte Carlo method, etc. can be employed. For example, the computer 150 can calculate the light fluence spatial distribution in the subject 100 by solving a light diffusion equation of formula (1).

[Formula (1)]

$$\frac{1}{c}\frac{\partial}{\partial t}\Phi(r, t) = -\mu_a \Phi(r, t) + \nabla \cdot (D\nabla\Phi(r, t)) + S(r, t) \qquad \text{formula (1)}$$

In formula (1), D is the diffusion coefficient, $\mu_a$ is the absorption coefficient, S is the incident intensity of irradiation light, $\Phi$ is the fluence of reaching light, r is the position, and t is the time.

Further, steps S330 and S340 can be executed using light of a plurality of wavelengths, and the calculation unit 151 can acquire absorption coefficient distribution information for each of the plurality of wavelengths of the light in steps S330 and S340. Then, the calculation unit 151 can acquire as photoacoustic image data spatial distribution information about the concentrations of substances of the subject 100 as spectral information based on the absorption coefficient distribution information corresponding to the light of the plurality of wavelengths. More specifically, the calculation unit 151 can acquire the spectral information using the signal data corresponding to the light of the plurality of wavelengths.

Alternatively, the computer 150 as the information processing apparatus that is an apparatus different from a modality can execute the image processing method according to the present exemplary embodiment. In this case, the computer 150 acquires image data generated in advance by the modality by reading the image data from a storage unit such as a picture archiving and communication system (PACS), and applies the image processing method according to the present exemplary embodiment to the image data. As described above, the image processing method according to the present exemplary embodiment is also applicable to image data generated in advance.

(Step S360: Photoacoustic Image Display)

The computer 150 as a display control unit generates a photoacoustic image based on the photoacoustic image data acquired in step S350 and causes the display unit 160 to display the photoacoustic image. Alternatively, the computer 150 may not only cause image data of subject information to be displayed as an image but also cause the numerical value of the subject information about a specific position in the image to be displayed. In step S360, a photoacoustic image that is prevented from having a decreased visibility due to body hair and moles can be generated and displayed. Step S360 will be described in detail below with reference to a flowchart illustrated in FIG. 7.

(Step S361: Determination of Position Having Image Value that is within Predetermined Range)

The computer 150 as a position acquisition unit determines a position (pixel or voxel) having an image value that is within the predetermined range in the photoacoustic image data generated in step S350, and stores in the storage unit 152 position information indicating the position.

The user can designate the predetermined range by inputting numerical values using the input unit 170, by operating a slider bar, or by designating a position on image data displayed on the display unit 160 to designate the image value of the position as the predetermined value. Alternatively, the user can designate the predetermined range by selecting a numerical value range designated by the user from a plurality of numerical value ranges.

Further, the computer 150 can acquire the predetermined range by reading the predetermined range stored in the storage unit 152. For example, in the case of an application to image data indicating the spatial distribution of the absorption coefficient when the observation region is a blood vessel, a value that is twice or more the normal absorption coefficient of the blood vessel can be set as a threshold value, and a numerical value range that is not less than the threshold value can be stored as the predetermined range in the storage unit 152.

Further, the computer 150 can determine the predetermined range by generating a histogram of the image values of the photoacoustic image data generated in step S350 and analyzing the histogram. The computer 150 detects a peak derived from an unnecessary structure from the histogram of the image values and determines as the predetermined range the numerical value range of the image values of a histogram distribution that includes the peak. For example, if the computer 150 acquires distributions having three peaks derived from background tissue, blood vessel, and body hair from the histogram of the image values, the computer 150 detects the distribution with the highest image value. The detected distribution is presumed to be the distribution derived from the body hair. Then, the computer 150 determines the numerical value range of the image values of the detected distribution as the predetermined range.

In step S361, the computer 150 can also acquire information indicating a position having an image value following the image value of the position that is within the predetermined range, as position information. At this time, the computer 150 also acquires information about a position having an image value that is not within the predetermined range, as position information, if the image value follows the image value of the position that is within the predetermined range. For example, first, the computer 150 determines a position having an image value that is within a numerical value range (first numerical value range) higher than a first threshold value. Then, the computer 150 acquires information indicating a position that follows the determined position and has an image value that is within a numerical value range (second numerical value range) higher than a second threshold value, which is smaller than the first threshold value, as position information. The user can designate at least one of the first and second numerical value ranges using the input unit 170.

Alternatively, the computer 150 can stratify the image values of the image data and determine a position having an image value that belongs to the predetermined group (predetermined range) among the stratified image value groups. For example, the computer 150 can stratify the image values of the positions in the image data into "large", "medium", and "small" groups and acquire position information indicating a position having an image value that belongs to the "large" group.

Figure 8A:
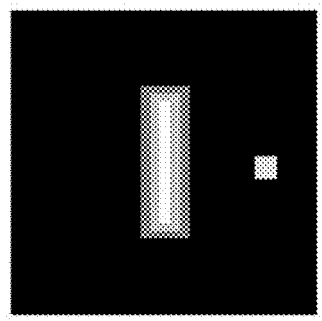
FIGS. 8A, 8B, 8C, 8D, and 8E illustrate the image processing method according to the first exemplary embodiment.
Figure 8B:
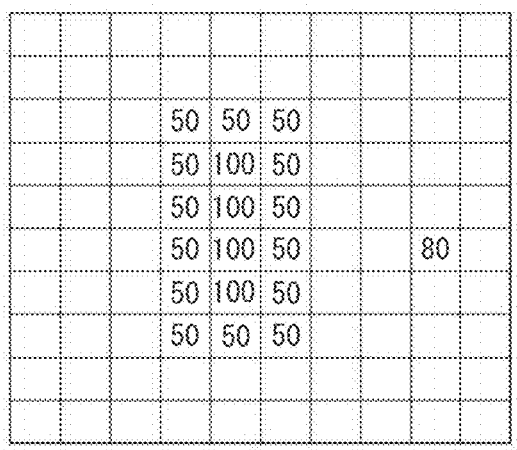

The case of an application of the image processing method according to the present exemplary embodiment to photoacoustic image data illustrated in FIG. 8A will be described below. FIG. 8B illustrates a spatial distribution in which the image values of the photoacoustic image data illustrated in FIG. 8A are specified by numerical values. The image values of pixels for which no numerical value is specified are zero.

Figure 8C:
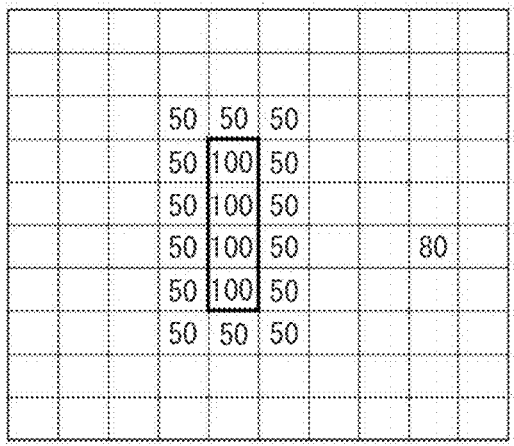

For example, the computer 150 determines positions having an image value of 100 or more in the photoacoustic image data illustrated in FIG. 8B. FIG. 8C illustrates the photoacoustic image data in which the positions (pixels) having an image value of 100 or more are specified by a thick line.

(Step S362: Determination of Neighborhood Position Neighboring Determined Position)

The computer 150 as a neighborhood position acquisition unit determines a neighborhood position neighboring the position determined in step S361 and stores neighborhood position information indicating the neighborhood position in the storage unit 152. In step S362, a position that is within a spatial range determined based on the position determined in step S361 can be determined as a neighborhood position.

The computer 150 can determine as a neighborhood position a position (pixel or voxel) adjacent to the position determined in step S361.

Further, the computer 150 can read range information indicating the spatial range stored in the storage unit 152 and determine as a neighborhood position a position that is within the spatial range based on the position determined in step S361. In the case in which body hair is determined as an unnecessary structure, a position that is within a range of 1 mm or more and 3 mm or less from the position determined in step S361 can be determined as a neighborhood position. For example, the computer 150 can determine as a neighborhood position a range of 2 mm or less from the position determined in step S361.

Further, the user can designate a spatial range using the input unit 170, and the computer 150 can determine as a neighborhood position a position that is within the spatial range designated by the user based on the position determined in step S361. Information indicating the spatial range can be information indicating the distance from the position determined in step S361. For example, the user can input a numerical value indicating the distance using the input unit 170 or can designate the distance by operating the slider bar. Further, the spatial range can be designated by selecting the spatial range designated by the user from a plurality of spatial ranges.

A position that is within an isotropic range from the position determined in step S361 can be determined as a neighborhood position, or a position that is within an anisotropic range from the position determined in step S361 can be determined as a neighborhood position. If an artifact occurs in a specific direction due to the properties of the apparatus, the range from the position determined in step S361 in the specific direction can be increased in the defining of a neighborhood position. Further, in the case of an apparatus having different resolutions in XYZ directions, a range to be determined as a neighborhood can be set anisotropically according to the resolutions. As described above, a range to be determined as a neighborhood is set anisotropically to realize more accurate discrimination of unnecessary structures.

The computer 150 can change the spatial range of the neighborhood used in step S362 in conjunction with the predetermined range used in step S361. For example, the spatial range of the neighborhood in step S362 can be increased as the threshold values with respect to the image values that are used in step S361 are increased. If the threshold values with respect to the image values that are used in step S361 are increased, fine discriminations between the observation region and unnecessary structures become possible, but only the central portions of the unnecessary structures can be identified. Thus, if the threshold values are increased in step S361, the spatial range of the neighborhood is increased in step S362 so that the entire unnecessary structures can be identified. On the other hand, the spatial range of the neighborhood can be decreased as the threshold values with respect to the image values that are used in step S361 are decreased.

Figure 8D:
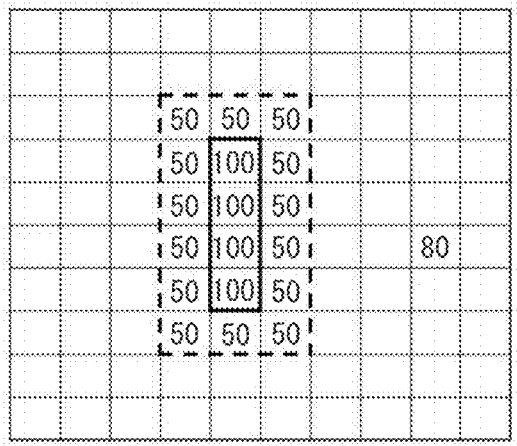

For example, the computer 150 determines positions (pixels) adjacent to the positions (pixels) having an image value of 100 or more as neighborhood positions neighboring the position determined in step S361. In FIG. 8D, the spatial range including the neighborhood positions (pixels) is specified by a dotted line. The area surrounded by the dotted line corresponds to an unnecessary image.

(Step S363: Display of Photoacoustic Image Based on Position Information and Neighborhood Position Information)

The computer 150 as a display control unit generates a photoacoustic image based on the photoacoustic image data acquired in step S350, the position information acquired in step S361, and the neighborhood position information acquired in step S362, and causes the display unit 160 to display the photoacoustic image.

The computer 150 may relatively reduce the lightness corresponding to the position determined in step S361 and the lightness corresponding to the neighborhood position determined in step S362 in the photoacoustic image to be displayed on the display unit 160. In the present exemplary embodiment, the lightness corresponding to the position defined by the position information and the lightness corresponding to the position defined by the neighborhood position information are set relatively lower than the lightness corresponding to other positions. Consequently, the photoacoustic images respectively corresponding to the position determined in step S361 and the neighborhood position determined in step S362 are displayed darker than the other positions. The images may be displayed based on the photoacoustic image data using any method capable of relatively reducing the lightnesses of the positions determined in steps S361 and S362.

For example, the lightnesses corresponding to the positions determined in steps S361 and S362 are determined as a first representative value (e.g., zero) and the lightnesses corresponding to the other positions as a second representative value (e.g., one). Alternatively, the lightness corresponding to the neighborhood position determined in step S362 is determined as a first representative value (e.g., zero), and the lightnesses corresponding to the other positions are determined according to the image values. Alternatively, the lightnesses corresponding to the positions determined in steps S361 and S362 are determined according to the image values, and the lightnesses corresponding to the other positions are also determined according to the image values. Even in this case, a first conversion coefficient for converting the image values corresponding to the positions determined in steps S361 and S362 into the lightness is set smaller than a second conversion coefficient for converting the image values corresponding to the other positions into the lightness.

Further, the computer 150 can determine the lightnesses corresponding to the positions determined in steps S361 and S362 based on information designated by the user. For example, the user can designate a representative value from a plurality of representative values using the input unit 170 to determine the designated representative value as the lightness.

Further, the computer 150 can relatively reduce the image values corresponding to the positions determined in steps S361 and S362 in the image data (corresponding to first image data) obtained in step S350. Consequently, image data (corresponding to second image data) with changed image values is acquired. Then, the computer 150 determines the lightness according to the image values of the second image data so that the positions having a reduced image value are displayed with a relatively reduced lightness.

In place of the adjustment of the lightness described above, the transparency (opacity) can be adjusted. In this case, increasing the transparency produces a similar effect to the effect produced by decreasing the lightness.

Further, the computer 150 can generate mask image data in which the image values are assigned to the positions determined in steps S361 and S362. Then, the computer 150 can execute masking processing on the photoacoustic image data using the mask image data and display an image based on the image data having undergone the masking processing. In this way, the image is displayed with reduced lightnesses corresponding to the positions determined in steps S361 and S362.

For example, first, the computer 150 generates mask image data in which zero is assigned to the image values corresponding to the positions determined in steps S361 and S362 and one is assigned to the image values corresponding to the other positions. Then, the computer 150 executes masking processing by multiplying the mask image data by the photoacoustic image data obtained in step S350. Further, for example, the computer 150 can generate mask image data having a Gaussian distribution in which zero is assigned to the image value of the position determined in step S361 and 0.5 is assigned to the image value of the neighborhood position that is determined in step S362 and located at the greatest distance from the position determined in step S361.

Further, the computer 150 can display the photoacoustic image having undergone the image processing in step S363 and the photoacoustic image not having undergone the image processing in step S363 in at least one of the display forms including parallel display, superimposition display, and switching display. Further, if the user selects a mode to display an image to which the image processing method according to the present exemplary embodiment is applied, the computer 150 can update the image displayed on the display unit 160 with the image to which the image processing method according to the present exemplary embodiment is applied.

Figure 8E:
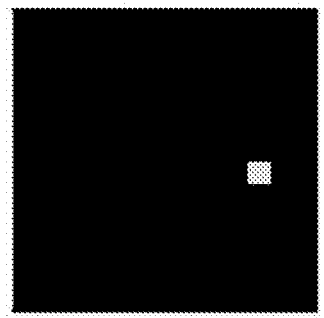

For example, in step S363, the computer 150 transmits to the display unit 160 a photoacoustic image in which the lightness corresponding to the area (pixel group) surrounded by the dotted line in FIG. 8D is set to zero and the lightnesses corresponding to the image values are assigned to the other positions. FIG. 8E illustrates a photoacoustic image that is consequently displayed on the display unit 160. From FIG. 8E to which the image processing method according to the present exemplary embodiment is applied, it is understood that the image of the body hair as an unnecessary image is selectively reduced. The image processing method according to the present exemplary embodiment is capable of improving the visibility of the image of the blood vessel that is an observation region.

Alternatively, the computer 150 can display a photoacoustic image to discriminate the positions determined in steps S361 and S362 from other positions instead of relatively reducing the lightnesses corresponding to the positions determined in steps S361 and S362. The positions determined in steps S361 and S362 and other positions can be discriminated by displaying the positions in different colors. Further, the positions determined in steps S361 and S362 can be discriminated by blinking. Any display form by which the positions determined in steps S361 and S362 can be discriminated visually from the other positions can be used.

The image processing method according to the present exemplary embodiment is applicable to the two- or three-dimensional spatial distribution of the subject information or is applicable to a projection image obtained by projecting a three-dimensional spatial distribution onto two-dimensions. In the case of the application to the three-dimensional spatial distribution (three-dimensional volume data), the three-dimensional volume data to which the image processing method according to the present exemplary embodiment is applied can be displayed on the display unit 160 by a given method. For example, the three-dimensional volume data to which the image processing method according to the present exemplary embodiment can be displayed by a method such as maximum intensity projection (MIP), minimum intensity projection (MinIP), or volume rendering (VR).

The photoacoustic image data to which the determination of a position having an image value that is within the predetermined range is applied and the photoacoustic image data to which the image value reduction is applied can be of the same type or different types. More specifically, the position determination processing in step S361 and the reduction processing in step S363 can be applied to different types of photoacoustic image data.

For example, the position determination processing may be applied to the photoacoustic image data (initial sound pressure distribution data) representing the spatial distribution of the initial sound pressure in step S361, and the reduction processing may be applied to the generated photoacoustic image data representing the spatial distribution of the absorption coefficient in step S363. In this case, in step S363, photoacoustic image data (absorption coefficient distribution data) representing the absorption coefficient is generated based on the initial sound pressure distribution data. Then, the image values of the absorption coefficient distribution data that correspond to the position determined based on the initial sound pressure distribution data and the neighborhood position neighboring the determined position are reduced. Further, the position determination processing may be applied to the initial sound pressure distribution data, and the reduction processing may be applied to the photoacoustic image data (concentration distribution data) representing the spatial distribution of the concentrations (oxygen saturation, etc.) of the substances.

As described above, the image values of unnecessary structures are reduced from image data in which the positions of the unnecessary structures are difficult to determine, using image data (initial sound pressure distribution data, etc.) in which the positions of the unnecessary structures are less difficult to determine from the image values.

Next, a signal processing method according to a second exemplary embodiment will be described below. In the present exemplary embodiment, sampling data having a signal level of signal data derived from a photoacoustic wave generated by light irradiation that is within a predetermined range is determined. Then, signal data is generated by relatively reducing the signal levels of the sampling data and sampling data that is temporally neighboring the sampling data. Then, image data is generated based on the signal data and displayed. The configuration of the photoacoustic apparatus according to the present exemplary embodiment is similar to that in the first exemplary embodiment, so detailed description thereof is omitted.

(Process for Acquiring Subject Information)

Next, a subject information acquisition method including the image processing according to the present exemplary embodiment will be described below with reference to FIG. 9. Steps S910 to S940 are similar to steps S310 to S340 in the first exemplary embodiment, so description of steps S910 to S940 is omitted.

(Step S950: Reduction of Signal Data Derived from Unnecessary Structure)

The computer 150 as a signal acquisition unit acquires signal data collected by the signal collection unit 140 by reading the signal data from the storage unit 152. Then, the computer 150 as a signal processing unit executes signal level reduction processing on the signal data. The sampling data determination processing for determining sampling data on which the signal level reduction is to be executed and the signal level reduction processing according to the present exemplary embodiment will be described below with reference to a detailed flowchart illustrating step S950 in FIG. 10.

(Step S951: Determination of Sampling Data Having Signal Level that is within Predetermined Range)

The computer 150 as a data determination unit determines sampling data having a signal level that is within the predetermined range among the signal data stored in the storage unit 152. Then, the computer 150 stores in the storage unit 152 position information indicating the temporal position (timing on the temporal axis of the signal data) of the sampling data.

The user may designate the predetermined range by inputting numerical values using the input unit 170 or by operating the slider bar. Alternatively, the user may designate the predetermined range by selecting a numerical value range designated by the user from a plurality of numerical value ranges. Further, the computer 150 may acquire the predetermined range by reading the predetermined range stored in the storage unit 152.

Further, the computer 150 may determine the predetermined range by generating a histogram of the signal level of the signal data that is acquired in step S940 and analyzing the histogram. The computer 150 detects a peak derived from an unnecessary structure from the histogram of the signal levels and determines as the predetermined range the numerical value range of the signal levels of a histogram distribution that includes the peak. For example, if the computer 150 acquires distributions having three peaks derived from background tissue, blood vessel, and body hair from the histogram of the signal levels, the computer 150 detects the distribution with the highest signal level. The detected distribution is presumed to be the distribution derived from the body hair. Then, the computer 150 determines the numerical value range of the signal levels of the detected distribution as the predetermined range.

Alternatively, the computer 150 may stratify the signal levels of the signal data and determine a temporal position having a signal level that belongs to the predetermined group (predetermined range) among the stratified signal level groups. For example, the computer 150 may stratify the signal levels of the sampling data of the signal data into "large", "medium", and "small" groups and acquire position information indicating a temporal position having a signal level that belongs to the "large" group.

(Step S952: Determination of Temporally Neighboring Sampling Data)

The computer 150 as a neighborhood data determination unit determines sampling data that temporally neighbors the sampling data determined in step S951 and stores in the storage unit 152 neighborhood position information indicating the temporal position of the sampling data. The pieces of sampling data corresponding to the temporal positions determined in step S951 and S952 will be reduction processing targets described below.

The computer 150 may determine as a temporally neighboring position a temporal position that is adjacent to the temporal position determined in step S951. More specifically, previous sampling data and subsequent sampling data with respect to the sampling data determined in step S951 may be determined as temporally neighboring sampling data.

Further, the computer 150 may read range information indicating the temporal range stored in the storage unit 152 and determine as a temporally neighboring position a temporal position that is within the temporal range based on the temporal position determined in step S951.

Further, the user may designate a temporal range using the input unit 170, and the computer 150 can determine as temporally neighboring data the data that is within the temporal range designated by the user based on the temporal position determined in step S951. The information indicating the temporal range may be information indicating the number of previous and subsequent samples with respect to the sampling data determined in step S951 and the sampling period. For example, the user may designate the number of samples or the sampling period by inputting numerical values indicating the number of samples or the sampling period using the input unit 170 or by operating the slider bar. Further, the user may designate the temporal range by selecting the temporal range designated by the user from a plurality of temporal ranges.

On one-dimensional signal data, data that is within the temporally isotropic range from the data determined in the step S951 may be determined as temporally neighboring data, or data that is within the temporally anisotropic range from the data determined in the step S951 may be determined as temporally neighboring data. If tailings occur in the reception signals due to phase characteristics of the transducers, data that is within the anisotropic temporal range with the temporally subsequent range being increased may be defined as temporally neighboring data. The temporally neighboring range is set anisotropically as described above to realize more accurate determination of data derived from unnecessary structure.

(Step S953: Signal Level Reduction)

The computer 150 as a signal processing unit reduces the signal level of the signal data corresponding to the unnecessary structure based on the signal data acquired in step S940, the position information acquired in step S951, and the neighborhood position information acquired in step S952. More specifically, the computer 150 relatively reduces the sampling data corresponding to the temporal positions determined in steps S951 and S952 with respect to the signal data (first signal data) stored in the storage unit 152. Then, signal data (second signal data) obtained as a result of the reduction processing is stored in the storage unit 152.

The computer 150 reduces the signal levels of the sampling data corresponding to the temporal positions determined in steps S951 and S952 whereas the computer 150 does not have to reduce the signal levels of sampling data corresponding to the other temporal positions. Further, the computer 150 may amplify the signal levels of sampling data corresponding to the other temporal positions while not changing the signal levels of the sampling data corresponding to the temporal positions determined in steps S951 and S952. Even in this case, it can be said that the signal levels of the sampling data corresponding to the temporal positions determined in steps S951 and S952 are relatively reduced.

As to the weighting regarding the reduction (reduction level), a predetermined value may be read from the storage unit 152 and determined, or the user may designate the weighting regarding the reducing using the input unit 170. The user may designate the weighting regarding the reduction by inputting numerical values using the input unit 170 or by operating the slider bar. Further, an image to which the weighting regarding the reduction that is changed based on the user instruction may be displayed on the display unit 160, and the user may give an instruction on the weighting regarding the reduction using the input unit 170 by checking the image.

Any type of signal processing may be executed by which the signal levels of the sampling data corresponding to the temporal positions determined in steps S951 and S952 are relatively reduced.

(Step S960: Photoacoustic Image Data Acquisition)

The computer 150 generates photoacoustic image data based on the signal data acquired in step S950 using a similar method to that used in step S350. Since information corresponding to the unnecessary structure is already reduced in step S950, information about the unnecessary structure contained in the photoacoustic image data acquired in step S960 is also reduced.

(Step S970: Photoacoustic Image Display)

The computer 150 transmits to the display unit 160 the photoacoustic image data acquired in step S960 and causes the display unit 160 to display the photoacoustic image data as a photoacoustic image. The computer 150 may cause the numerical value of the subject information on a specific position of the image to be displayed in addition to causing the image data of the subject information to be displayed as the image. Further, the computer 150 may cause the photoacoustic image having undergone the signal processing according to the present exemplary embodiment and the photoacoustic image not having undergone the signal processing according to the present exemplary embodiment to be displayed in at least one of the display forms including parallel display, superimposition display, and switching display.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-022468, filed Feb. 9, 2017, which is hereby incorporated by reference herein in its entirety.

What is claimed is:

1. An information processing apparatus comprising:
   a memory storing a program; and
   one or more processors which, by executing the program, function as:
   a first image acquisition unit configured to acquire first image data derived from a photoacoustic wave generated by a light irradiation;
   a position acquisition unit configured to acquire position information indicating a position in the first image data having an image value that is within a predetermined range;
   a neighborhood position acquisition unit configured to acquire range information indicating a spatial range based on a user instruction, and neighborhood position information indicating a neighborhood position that is within the spatial range with reference to the position based on the position information; and
   a display control unit configured to acquire second image data by reducing an image value of the first image data that corresponds to the position acquired by the position acquisition unit and the image value of the first image data that corresponds to the neighborhood position acquired by the neighborhood position acquisition unit, and cause a display unit to display an image based on the second image data.

2. The information processing apparatus according to claim 1, wherein the display control unit causes the display unit to display the image with a relatively low lightness corresponding to the position and with a relatively low lightness corresponding to the neighborhood position, based on the first image data, the position information, and the neighborhood position information.

3. The information processing apparatus according to claim 1, wherein the display control unit causes the display unit to display the image based on the first image data, the position information, and the neighborhood position information so that the position and the neighborhood position are discriminable from another position.

4. The information processing apparatus according to claim 1,
   wherein the first image data is three-dimensional volume data, and
   wherein the display control unit causes the display unit to display the image that is two-dimensional based on the first image data, the position information, and the neighborhood position information.

5. An information processing apparatus comprising:
   a memory storing a program; and
   one or more processors which, by executing the program, function as:
   a first image acquisition unit configured to acquire first image data derived from a photoacoustic wave generated by a light irradiation;
   a position acquisition unit configured to acquire position information indicating a position in the first image data having an image value that is within a predetermined range;
   a neighborhood position acquisition unit configured to acquire range information indicating a spatial range based on a user instruction, and neighborhood position information indicating a neighborhood position that is within the spatial range with reference to the position based on the position information;
   a second image acquisition unit configured to acquire second image data by reducing an image value of the first image data that corresponds to the position acquired by the acquisition unit and the image value of the first image data that corresponds to the neighborhood position acquisition unit; and
   a display control unit configured to cause a display unit to display an image based on the second image data.

6. The information processing apparatus according to claim 5,
   wherein the first image data is image data representing a spatial distribution of an initial sound pressure, and
   wherein the second image data is image data representing a spatial distribution of an absorption coefficient or a concentration of a substance.

7. The information processing apparatus according to claim 5,
   wherein the display control unit acquires third image data by relatively reducing the image value of the second image data that corresponds to the position and the image value of the second image data that corresponds to the neighborhood position, based on the second image data, the position information, and the neighborhood position information, and
   wherein the display control unit causes the display unit to display the image with a lightness according to an image value of the third image data.

8. The information processing apparatus according to claim 5, wherein the display control unit causes the display unit to display the image with a relatively low lightness corresponding to a position and with a relatively low lightness corresponding to the neighborhood position, based on the second image data, the position information, and the neighborhood position information.

9. The information processing apparatus according to claim 5, wherein the display control unit causes the display unit to display the image based on the second image data, the position information, and the neighborhood position information so that the position and the neighborhood position are discriminable from another position.

10. The information processing apparatus according to claim 5,
    wherein the second image data is three-dimensional volume data, and
    wherein the display control unit causes the display unit to display the image that is two-dimensional based on the second image data, the position information, and the neighborhood position information.

11. The information processing apparatus according to claim 5,
wherein the neighborhood position acquisition unit acquires range information indicating a spatial range based on a user instruction, and
wherein the neighborhood position acquisition unit acquires, based on the position information and the range information the neighborhood position information indicating as the neighborhood position, a position that is within the spatial range with reference to the position.

12. The information processing apparatus according to claim 1, wherein the first image acquisition unit acquires the first image data by reading the first image data from a storage unit.

13. The information processing apparatus according to claim 5, wherein the first image acquisition unit acquires the first image data by reading the first image data from a storage unit.

14. An information processing method comprising:
acquiring first image data derived from a photoacoustic wave generated by a light irradiation;
determining a position in the first image data having an image value that is within a predetermined range;
acquiring range information indicating a spatial range based on a user instruction and neighborhood position information indicating a neighbor position that is within a spatial range with reference to the position based on the position information; and
displaying an image based on second image data acquired by reducing an image value of the first image data with a relatively low lightness corresponding to the acquired position and with a relatively low lightness corresponding to a neighborhood position neighboring the position.

15. An information processing method comprising:
acquiring first image data derived from a photoacoustic wave generated by a light irradiation;
determining a position in the first image data having an image value that is within a predetermined range;
acquiring range information indicating a spatial range based on a user instruction and neighborhood position information indicating a neighbor position that is within a spatial range with reference to the position based on the position information;
acquiring second image data by reducing an image value of the first image data that corresponds to the acquired position, and the image value of the first image data corresponding to a neighborhood position neighboring the position; and
displaying an image based on the second image data.

16. A non-transitory storage medium that stores a program for causing a computer to execute the information processing method according to claim 14.

17. A non-transitory storage medium that stores a program for causing a computer to execute the information processing method according to claim 15.

* * * * *